United States Patent
Kannusamy et al.

(10) Patent No.: US 11,648,242 B2
(45) Date of Patent: May 16, 2023

(54) PHARMACEUTICAL COMPOSITION COMPRISING PIMAVANSERIN, PROCESS OF PREPARATION AND USE THEREOF

(71) Applicant: Aurobindo Pharma Ltd., Hyderabad (IN)

(72) Inventors: Saravanan Kannusamy, Hyderabad (IN); Prabhakaran Chakkirala, Hyderabad (IN); Rakesh Sarkar, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 95 days.

(21) Appl. No.: 17/119,250

(22) Filed: Dec. 11, 2020

(65) Prior Publication Data

US 2021/0177822 A1  Jun. 17, 2021

(30) Foreign Application Priority Data

Dec. 12, 2019 (IN) .......................... IN201941051447

(51) Int. Cl.
| | | |
|---|---|---|
| *A61K 31/4468* | (2006.01) | |
| *A61K 9/48* | (2006.01) | |
| *A61K 9/00* | (2006.01) | |

(52) U.S. Cl.
CPC ........ *A61K 31/4468* (2013.01); *A61K 9/0053* (2013.01); *A61K 9/485* (2013.01); *A61K 9/4833* (2013.01); *A61K 9/4858* (2013.01); *A61K 9/4866* (2013.01)

(58) Field of Classification Search
CPC .............. A61K 31/4468; A61K 9/0053; A61K 9/4833; A61K 9/485; A61K 9/4858; A61K 9/4866
See application file for complete search history.

(56) References Cited

U.S. PATENT DOCUMENTS

| 6,451,343 | B1 * | 9/2002 | Glinecke | ................ | A61P 43/00 |
|---|---|---|---|---|---|
| | | | | | 424/478 |
| 10,449,185 | B2 * | 10/2019 | Tejwani | ............... | A61K 9/2009 |
| 10,953,000 | B2 * | 3/2021 | Parkinson | ............ | A61K 9/0053 |
| 2007/0264330 | A1 * | 11/2007 | Ragnar-Tolf | ......... | A61K 9/2059 |
| | | | | | 424/464 |
| 2020/0237739 | A1 * | 7/2020 | Coate | ................... | A61K 31/473 |
| 2021/0161880 | A1 * | 6/2021 | Foff | ..................... | A61K 31/135 |
| 2022/0016101 | A1 * | 1/2022 | Burstein | .............. | A61K 31/343 |

* cited by examiner

*Primary Examiner* — Robert A Wax
*Assistant Examiner* — Olga V. Tcherkasskaya
(74) *Attorney, Agent, or Firm* — Jay R Akhave

(57) ABSTRACT

The present invention relates to prepare pharmaceutical compositions comprising pimavanserin or a pharmaceutically acceptable salt thereof, processes for manufacturing said pharmaceutical compositions comprising pimavanserin or a pharmaceutically acceptable salt thereof. Also pharmaceutical compositions comprising pimavanserin or a pharmaceutically acceptable salt thereof for the treatment of hallucinations and delusions associated with Parkinson's disease psychosis.

5 Claims, 2 Drawing Sheets

PHARMACEUTICAL COMPOSITION COMPRISING PIMAVANSERIN, PROCESS OF PREPARATION AND USE THEREOF

CROSS REFERENCE TO RELATED APPLICATIONS

This application claims priority from an Indian Patent Application IN 201941051447 filed on Dec. 12, 2019.

FIELD OF THE INVENTION

Provided herein are pharmaceutical compositions comprising pimavanserin or a pharmaceutically acceptable salt thereof, processes for manufacturing said composition. Also provided herein are pharmaceutical compositions comprising pimavanserin or a pharmaceutically acceptable salt thereof for the treatment of hallucinations and delusions associated with Parkinson's disease psychosis.

BACKGROUND OF THE INVENTION

Pimavanserin tartrate capsule product got approved by FDA and sold under the trade name NUPLAZID® The chemical name of Pimavanserin tartrate is urea, N-[(4-fluorophenyl) methyl]-N-(1-methyl-4-piperidinyl)-N'-[[4-(2methylpropoxy) phenyl] methyl]-, (2R, 3R)-2, 3-dihydroxybutanedioate (2:1). Pimavanserin tartrate is freely soluble in water. Its molecular formula is $(C_{25}H_{34}FN_3O_2)_2 \cdot C_4H_6O_6$ and its molecular weight is 1005.20 (tartrate salt). The chemical structure is:

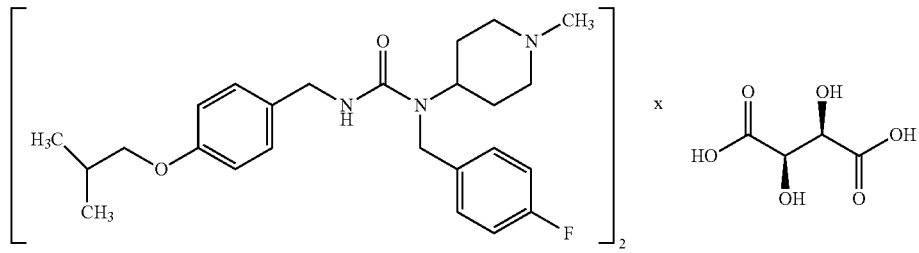

Patients suffering from neurodegenerative diseases, such as Parkinson's disease are at a risk of non-compliance when administered a drug of too large size, or if taken as more than one tablet per day as said patients often have difficulty swallowing. Pimavanserin tartrate got approved under trade name NUPLAZID® and sold as tablets containing 20 mg pimavanserin tartrate (equivalent to 17 mg pimavanserin), taken as two tablets once a day. However, the product got discontinued later. Pimavanserin tartrate is also available in the USA as 34 mg capsules for oral administration. In addition to the active ingredient, pimavanserin tartrate, each capsule contains the following inactive ingredients: magnesium stearate and microcrystalline cellulose. Additionally, the following inactive ingredients are present as components of the capsule shell: black iron oxide, FD&C blue #1, hypromellose, titanium dioxide, and yellow iron oxide.

U.S. Pat. No. 10,449,185 of ACADIA Pharmaceuticals Inc. covers a pharmaceutically acceptable capsule for orally delivering 34 mg of pimavanserin to a patient, wherein the capsule has a capsule shell with a capsule shell size 3 or 4, that encapsulates a blended pimavanserin composition comprising: 40 mg granulated pimavanserin tartrate having a particle size distribution (D90) of 180 to 340 μm, wherein the bulk density of the granulated pimavanserin is 0.4 to 0.6 g/ml as determined by USP<616>, method 1; 59 mg microcrystalline cellulose having a particle size distribution (D90) of 180 to 340 μm; and 1 mg magnesium stearate; wherein the particle size distribution is measured using laser light scattering with a Malvern Mastersizer 2000 LLS PS system, a Scirocco 2000 dry dispersion unit and a sample size of 2 to 10 g. U.S. Pat. No. 10,449,185 acknowledge the problems of Pimavanserin manufactured following conventional techniques has low bulk density and poor flowability and a tendency to clump, which will adversely impact reproducibility and quantitative accurate filling of capsules during the manufacturing process. Therefore, U.S. Pat. No. 10,449,185 described embodiments with the use of pimavanserin, which is the crystalline form of the tartrate salt of pimavanserin Form A or Form C. Also described the processes to manufacture capsules comprising 5-34 mg pimavanserin. It was found that a 100% pimavanserin high-shear granulation was possible by using only small water quantities, often large quantities of water and a binder conventionally used in high-shear granulation. In order for a small quantity of water to be effective, the distribution of the water should be finely divided providing small points of localized wetting of pimavanserin. Localized wetting is considered wetting of an immediate area around the water droplets. Also U.S. Pat. No. 10,449,185 disclose that the risk of changing the crystalline form of pimavanserin (e.g. changing pimavanserin into amorphous forms), could result in slow dissolution when administered to a patient.

IN201721018144 of Lupin Ltd discloses a stable amorphous pimavanserin tartrate premix comprising pimavanserin tartrate and at least one pharmaceutically acceptable excipient. The stable amorphous pimavanserin tartrate premix was prepared by mixing the pimavanserin tartrate with at least one pharmaceutical acceptable excipient selected from silicon dioxide or colloidal silicon dioxide by following method: (i) adding pimavanserin tartrate in one or more solvent; (ii) optionally heating the mixture; (iii) adding the excipient, and (iv)isolating pimavanserin tartrate premix.

There exists few problems in formulation development of pimavanserin with the use of crystalline forms and/or aforementioned processes. Hence, there is an unmet need to develop simple pimavanserin compositions which are free of manufacturing problems and also have comparative dissolution profiling and bioequivalence with that of commercially available pimavanserin tartrate capsules.

SUMMARY OF INVENTION

Provided herein are pharmaceutical compositions comprising 5-34 mg pimavanserin (equivalent to 6-40 mg amorphous pimavanserin tartrate), or a pharmaceutically acceptable salt thereof.

Provided herein are also pharmaceutical compositions consisting of 5-34 mg pimavanserin (equivalent to 6-40 mg amorphous pimavanserin tartrate) or a pharmaceutically acceptable salt thereof, a filler(s), glidant(s) and lubricant(s).

Provided herein are also processes for manufacturing pharmaceutical compositions comprising 5-34 mg pimavanserin (equivalent to 6-40 mg amorphous pimavanserin tartrate) comprising:
i) Blending amorphous pimavanserin tartrate with the pharmaceutically acceptable excipient(s) selected from diluent(s), glidant(s) or combinations thereof;
ii) Lubricating the blend with the addition of lubricant(s);
iii) Filling the dry blend into suitable empty capsule shells.

Provided herein are pharmaceutical compositions comprising 5-34 mg pimavanserin (equivalent to 6-40 mg amorphous pimavanserin tartrate), for the treatment of hallucinations and delusions associated with Parkinson's disease psychosis.

DETAILED DESCRIPTION OF THE INVENTION

Figure 1:
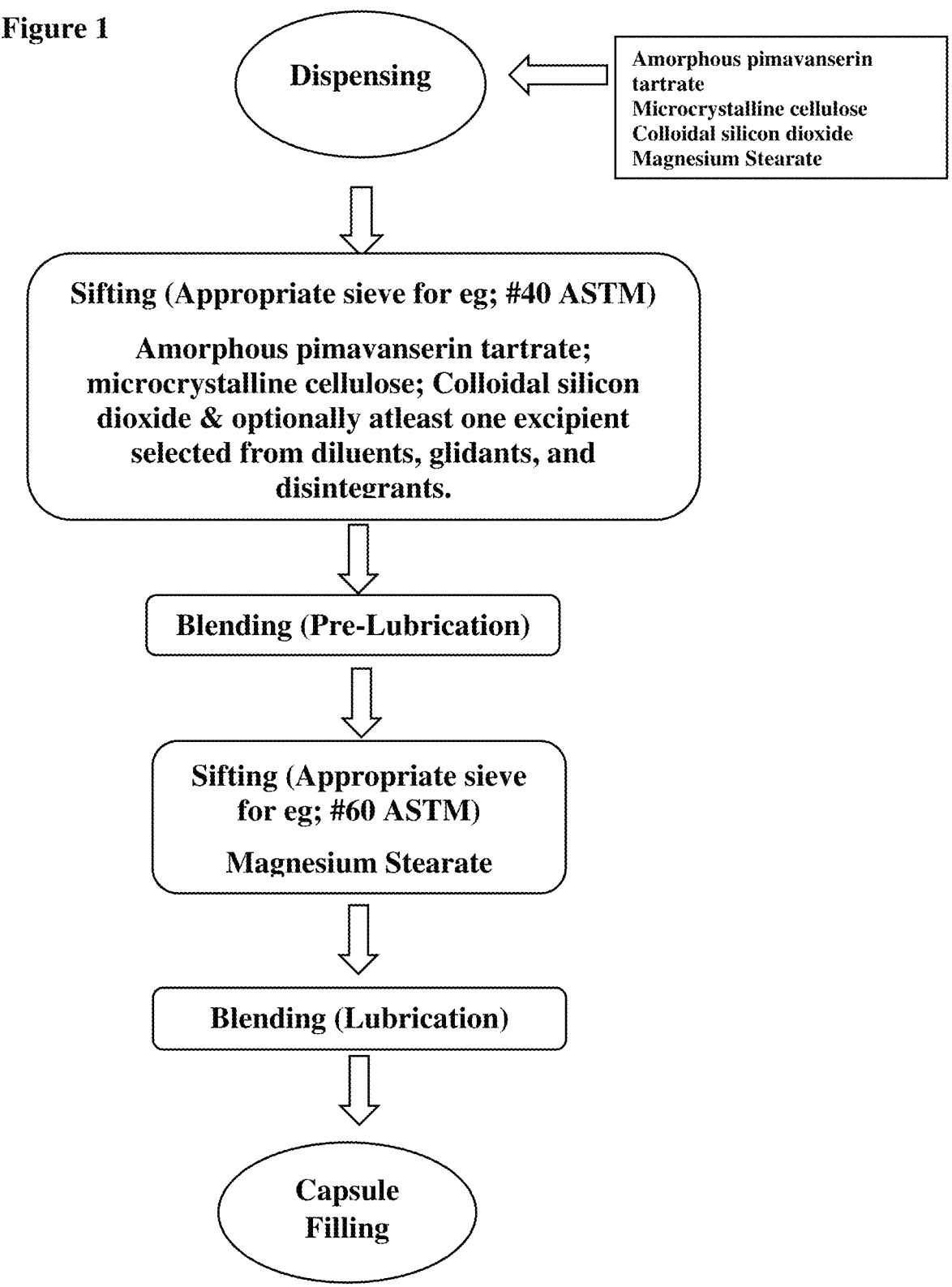
FIG. 1: schematically discloses a process flow chart for capsule filling pimavanserin.
Figure 2:
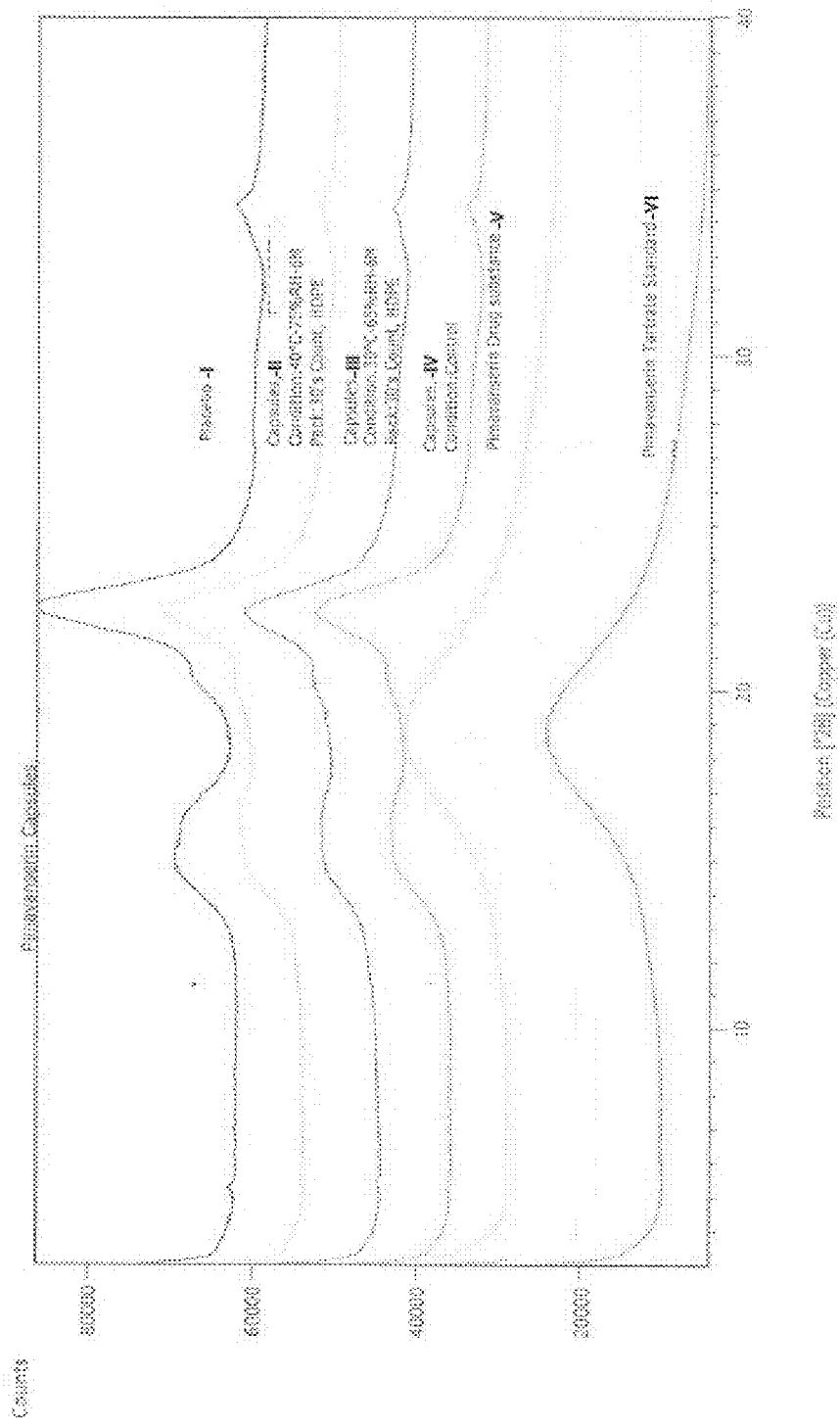
FIG. 2 illustrates the X-ray powder diffraction pattern of the following:
I. indicates the X-ray powder diffraction pattern of placebo of example 1A.
II. indicates the X-ray powder diffraction pattern of pimavanserin tartrate capsules of example 1 stored at 40±2° C./75±5% Relative Humidity (RH) for 6 months in HDPE bottle.
III. indicates the X-ray powder diffraction pattern of pimavanserin tartrate capsules of example 1 stored at 30±2° C./65±5% RH for 6 months in HDPE.
IV. indicates the X-ray powder diffraction pattern of pimavanserin tartrate capsules prepared according to example 1 at initial stage.
V. indicates the X-ray powder diffraction pattern of input API [Amorphous pimavanserin tartrate [API].
VI. indicates the X-ray powder diffraction pattern of pimavanserin tartrate (Standard).

As used herein, "a" or "an" means one or more unless otherwise specified.

Open terms such as "include," "including," "contain," "containing" and the like mean "comprising".

The term "treatment" or "treating" refers to administering a therapy in an amount, manner, or mode effective to improve a condition, symptom, or parameter associated with a disorder.

The term "Administering" or "administration" means providing a drug to a patient in a manner that is pharmacologically useful.

The term "or" can be conjunctive or disjunctive.

The term "% by weight" is based on the weight of the total composition.

As used herein, "pharmaceutical composition" refers to a composition of one or more active pharmaceutical ingredient(s) alone, or administered with other chemical components, such as diluents, binders, lubricants, pharmaceutical flow agents, and/or other excipients, e.g. for forming a unit dose, such as a capsule, a tablet etc.

As used herein, "pharmaceutically acceptable excipient" defines a diluent, glidant, lubricant, binder, disintegrant or any other excipient that does not abrogate the biological activity and properties of the pharmaceutically active compound.

The term "an effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

The term "therapeutically effective amount" means an effective dose (ED) or effective concentration (EC) of active ingredient or a drug that produces a biological response.

The terms screen, screening, delump, delumping, dry milling, and sizing are used interchangeably herein. These terms refer to separation according to size.

The term "granulation" as used herein, and as conventionally used in the pharmaceutical industry, refers to the act or process in which primary powder particles are made to adhere to form larger, multiparticle entities called granules.

The terms "granulated pimavanserin" and "pimavanserin granulation" are used interchangeably herein.

The term "blending" refers to the mixing of pharmaceutical ingredients to form a mixture of the ingredients, e.g. active pharmaceutical ingredient (API) and diluent, as defined by pharmaceutical specifications in the compendial references using a variety of equipment such as, but not limited to, '"V"-blenders, bin-blenders, cone-blenders.'

The term "encapsulation" refers to a range of techniques used to enclose medicines in a shell, e.g. a two-piece capsule, such as a two-piece hard shell capsule. The capsule referred to herein may be taken orally. Capsules may be designed with a telescoping cap and body manufactured from e.g. gelatin or cellulose.

As used herein, an "excipient" refers to an inactive ingredient that is added to a pharmaceutical composition to provide, without limitation, bulk, consistency, stability, binding ability, lubrication, disintegrating ability, etc., to the composition.

As used herein, a "diluent", "bulking agent" and "filler" refer to an ingredient (excipient) in a pharmaceutical composition that lacks pharmacological activity but may be pharmaceutically necessary or desirable, e.g. to enhance or improve the properties of the pharmaceutical blend for manufacturing or physiological purposes. For example, a diluent or filler may be used to increase the bulk of a potent drug whose mass is too small for manufacture or administration. Examples of the diluent or filler also include cellulose derivatives, such as microcrystalline cellulose or wood cellulose, lactose, sucrose, starch, pregelatinized starch, dextrose, mannitol, fructose, xylitol, sorbitol, corn starch, modified corn starch, inorganic salts such as calcium carbonate, calcium phosphate, dicalcium phosphate, calcium sulfate, dextrin/dextrates, maltodextrin, and compressible sugars. In certain embodiments, the composition of the present invention includes microcrystalline cellulose as diluent or filler.

As used herein, a "binder" or is an excipient holding the ingredients together, and forming granules or tablets with required mechanical strength, and may give volume to the formulation. Specific examples of binders are mono-, di-, and poly-saccharides and derivatives thereof; sugar alcohols such as xylitol, sorbitol or maltitol; protein, such as; synthetic polymers, such as polyvinylpyrrolidone (PVP), polyethylene glycol (PEG). Binders are classified according to their application, e.g. solution binders are dissolved in a solvent (for example water or alcohol may be used in wet granulation processes). Examples include gelatin, cellulose, cellulose derivatives, polyvinylpyrrolidone, starch, sucrose and polyethylene glycol. Dry binders are added to the powder blend, either after a wet granulation step, or as part of a direct powder compression (DC) formula. Examples include cellulose, methyl cellulose, polyvinylpyrrolidone and polyethylene glycol.

As used herein a "lubricant" refers to an excipient which for example prevents ingredients and excipients to lump together, and/or sticking to the capsule filling machine. A lubricant may also ensure that the formation, filing and ejection of the capsule can occur, for example by lowering friction. Examples of lubricants are talc, silicon dioxide (silica), fatty acids or fatty acid salts, such as magnesium stearate, sodium stearate fumarate, stearic acid, etc.

As used herein a "disintegrant" refers to an excipient which disintegrate a pharmaceutical preparation on contact with an aqueous fluid. Examples of disintegrant suitable for use herein include croscarmellose sodium, crospovidone, starch, potato starch, pregelatinized starch, corn starch, sodium starch glycolate, low substituted hydroxypropyl cellulose and other known disintegrants.

As used herein a "glidant" refers to an excipient which is added to a powder to improve its flowability. Examples of glidant suitable for use herein include talc, colloidal silicon dioxide, silicic acid, cornstarch, calcium silicate, magnesium carbonate, magnesium oxide, magnesium silicate, starch, castor wax. In certain embodiments of the present invention the composition includes colloidal silicon dioxide as glidant.

As used herein, "Uniformity of dosage units" refers according to USP <905>.

As used herein, "dissolution" refers according to USP <711> dissolution apparatus 1 and the acceptance criteria is that at least 80% of the pimavanserin released within 30 minutes in accordance with USP <711> dissolution apparatus 1.

As used herein, the term "stable" or "stability" as used herein refers to a pharmaceutical composition that retains its physical stability, polymorphic stability and/or chemical stability and comply with the standard stability criteria given in USP/EP compendia.

Compounds:—

Pimavanserin, which is also known as N-(1-methylpiperidin-4-yl)-N-(4-fluorophenylmethyl)-N'-(4-(2-methylpropyl-oxy)phenylmethyl)carbamide, N-[(4-fluorophenyl)methyl]-N-(1-methyl-4-piperidinyl)-N'-[[4-(2-methylpropoxy)phenyl]methyl]-urea, 1-(4-fluorobenzyl)-1-(1-methylpiperidin-4-yl)-3-[4-(2-methylpropoxy)benzy-l]urea, or ACP-103. WO2001044191 & WO2001066521 disclose a novel compound 4-aminopiperidine derivatives (pimavanserin) and use of compound for treating pathological conditions or diseases wherein one (or several) somatostatin receptor(s) is/are involved. WO2004064738 discloses the use of a specific novel compound (pimavanserin) and related serotonin 2A/2C receptor inverse agonists to treat variety of human neurodegenerative diseases including Parkinson's disease, Huntington's Disease, Lew Body Dementia and Alzheimer's Disease. Col.19, In 27-31 of U.S. Pat. No. 7,732,615 discloses amorphous pimavanserin and/or amorphous pimavanserin tartrate and processes for preparation thereof.

As used herein, "pharmaceutically acceptable salt" refers to a salt of a compound that does not abrogate the biological activity and properties of the compound. Pharmaceutical salts can be obtained by reaction of a compound disclosed herein with an acid or base. Base-formed salts include, without limitation, ammonium salt ($NH^+_4$); alkali metal, such as, without limitation, sodium or potassium, salts; alkaline earth, such as, without limitation, calcium or magnesium, salts; salts of organic bases such as, without limitation, dicyclohexylamine, piperidine, piperazine, methylpiperazine, N-methyl-D-glucamine, diethylamine, ethylenediamine, tris(hydroxymethyl)methylamine; and salts with the amino group of amino acids such as, without limitation, arginine and lysine. Useful acid-based salts include, without limitation, acetates, adipates, aspartates, ascorbates, benzoates, butyrates, caparate, caproate, caprylate, camsylates, citrates, decanoates, formates, fumarates, gluconates, glutarate, glycolates, hexanoates, laurates, lactates, maleates, nitrates, oleates, oxalates, octanoates, propionates, palmitates, phosphates, sebacates, succinates, stearates, sulfates, sulfonates, such as methanesulfonates, ethanesulfonates, p-toluenesulfonates, salicylates, tartrates, and tosylates. Pharmaceutically acceptable solvates and hydrates are complexes of a compound with one or more solvent of water molecules, or 0.5 to about 100, or 1 to about 100, or 1 to about 10, or one to about 2, 3 or 4, solvent or water molecules.

In particular embodiments, the present invention provides oral pharmaceutical compositions comprising of amorphous pimavanserin and/or amorphous pimavanserin tartrate.

In the present invention the native amorphous pimavanserin tartrate is having a particle size distribution ($D_{90}$) of less than 200 μm. In particular embodiments, the present invention the native amorphous pimavanserin tartrate is having a particle size distribution ($D_{90}$) of 75 to 180 μm and more preferably of 150 to 180 μm.

In the present invention the bulk density of the native amorphous pimavanserin tartrate is <0.4 g/ml and preferably at about 0.3 g/ml to less than 0.4 g/ml.

In certain embodiments, the present invention provides oral pharmaceutical compositions comprising 5-34 mg pimavanserin (equivalent to 6-40 mg amorphous pimavanserin tartrate), or a pharmaceutically acceptable salt thereof.

In a particular embodiments, the present invention provides a capsule comprising 5-34 mg pimavanserin (equivalent to 6-40 mg amorphous pimavanserin tartrate), or a pharmaceutically acceptable salt thereof.

In a particular embodiments, the present invention provides a capsule comprising 5-34 mg pimavanserin (equivalent to 6-40 mg amorphous pimavanserin tartrate) or a pharmaceutically acceptable salt thereof, a filler(s), glidant(s) and lubricant(s).

In particular embodiments, the present invention provides a capsule size 3 or 4 comprising 5-34 mg amorphous pimavanserin tartrate, microcrystalline cellulose, colloidal silicon dioxide and magnesium stearate.

In particular embodiments, the present invention provides a capsule size 3 or 4 comprising 5-34 mg amorphous pimavanserin tartrate, microcrystalline cellulose, colloidal silicon dioxide and magnesium stearate, wherein the composition is not a granulated pimavanserin and uniformity of the capsule dosage units is not more than 15.0. In preferred embodiments, the uniformity of the capsule dosage units is less than 10.0.

In a particular embodiments, the present invention provides a processes for manufacturing a capsule comprising 5-34 mg pimavanserin (equivalent to 6-40 mg amorphous pimavanserin tartrate):
i) Blending amorphous pimavanserin tartrate with the pharmaceutically acceptable excipients selected from diluent(s), glidant(s) or combinations thereof;
ii) Lubricating the blend with the addition of lubricant(s);
iii) Filling the dry blend into empty capsule shells.

Inventors of the present invention surprisingly found that the invention compositions are simple and easy to manufacture with no problems of flow property, encapsulation and had achieved highly reliable and precise content uniformity of capsule dosage units. Further, the dissolution profiling of the invention compositions are comparable to that of commercially available pimavanserin tartrate capsules. The inventors surprisingly acknowledged that these results were achieved without any of the below mentioned techniques. Instead the inventors of the present invention unexpectedly found that the direct/dry blending of native amorphous pimavanserin tartrate (API) with excipients gives the desirable results.
1. Dry granulation.
2. Conventional Wet granulation.
3. Wet granulation with lower quantities of water as taught under U.S. Ser. No. 10/449,185.
4. Use of Crystalline pimavanserin tartrate.
5. Use of pre-treatment of native pimavanserin tartrate (API).

In a particular embodiments, the present invention provides oral pharmaceutical compositions comprising 5-34 mg pimavanserin (equivalent to 6-40 mg amorphous pimavanserin tartrate), for the treatment of hallucinations and delusions associated with Parkinson's disease psychosis.

The following examples are intended to serve as illustrations of the present invention only and do not restrict the scope of the invention in any manner whatsoever.

EXAMPLES

Example 1

| Sr. No | Ingredients | Example-1 Quantity/ Capsule (mg) | Example-1A Quantity/ Capsule (mg) |
|---|---|---|---|
| 1 | Pimavanserin tartrate | 40.00 | — |
| 2 | Microcrystalline Cellulose | 55.00 | 55.00 |
| 3 | Colloidal silicon dioxide | 4.00 | 4.00 |
| 4 | Magnesium Stearate | 1.00 | 1.00 |
| | Total fill weight for Size 4 | 100.00 | 60.00 |

Manufacturing Procedure:

Step 1: Pimavanserin tartrate, microcrystalline cellulose and colloidal silicon dioxide were co-sifted.

Step 2: Materials of step 1 were re-sifted through specific sieve size.

Step 3: Sifted material of step 2 was blended with magnesium stearate for 5 minutes.

Step 4: Filled the blend of step 3 into empty capsule shells.

The native amorphous pimavanserin tartrate of example 1 was having a particle size distribution (D90) of about 100 μm and the bulk density of 0.374 g/ml.

Long term stability data for capsules containing 34 mg pimavanserin, 55 mg microcrystalline cellulose, 4 mg colloidal silicon dioxide and 1 mg magnesium stearate at 6 months were determined using standard procedures such as actual or simulated storage under open conditions at 30° C.±2° C./65%±5% RH, e.g. as outlined in WHO Technical Report Series, No. 953, 2009, Annex 2, and the following observations and determinations were made:

| | Comparative data between pimavanserin compositions: | | |
|---|---|---|---|
| S.no | Parameters | Example-1 | Comparative example [Data retrieved/taught under Example 1 of US10449185] |
| 1. | Nature of API | Amorphous pimavanserin tartrate | Crystalline Form C of pimavanserin tartrate. |
| 2. | Bulk density | 0.374 g/ml (<0.4 g/ml) | 0.4 to 0.6 g/ml |
| 3. | Particle size distribution of API | Amorphous pimavanserin tartrate having a particle size distribution (D90) of about 100 μm. | Granulated pimavanserin tartrate having a particle size distribution (D90) of 180 to 340 μm. |
| 4. | Manufacturing process | Direct blending and encapsulation. | Wet granulation method with little quantities of water as taught in US10449185. |
| 5. | Appearance | Unchanged | Unchanged |
| 6. | Description of the capsule size | Capsule size 4 | Capsule size 4 |
| 7. | Content Uniformity | 7.1 (Not more than 15) | Not more than 15 |
| 8. | Assay | 100 ± 2% | 100 ± 2% |
| 9. | Total impurities | <1% (At initial stage) | <1% (At initial stage) |
| 10. | Dissolution | At least 80% of the pimavanserin is released from the composition within 30 minutes upon in vitro dissolution testing according to USP<711> (apparatus 1 (basket apparatus). | At least 80% of the pimavanserin is released from the composition within 30 minutes upon in vitro dissolution testing according to USP<711> (apparatus 1 (basket apparatus). |

| | | Comparative data between pimavanserin compositions: | |
|---|---|---|---|
| S.no | Parameters | Example-1 | Comparative example [Data retrieved/taught under Example 1 of US10449185] |
| 11. | Polymorphic stability | Time Initial<br>30 ± 2° C./65 ± 5% RH; 6 Months<br>40 ± 2° C./75 ± 5% RH; 6 Months | Example 1 Amorphous (Figure 1) Amorphous (Figure 1) Amorphous (Figure 1) | X-ray powder diffraction patterns for the granulations correspond to pimavanserin tartrate form C were stable at (25 ± 2° C./60 ± 5% RH; 12 Months). |

Simpler and cheaper dry blending process would be expected to have disadvantages of poor flow and resulting poor formulation bulk density. However, the use of amorphous Pimavaserin of a lower D90 particle size distribution of about 100 microns with the simpler dry blending process surprisingly results in a formulation that can be successfully filled at high manufacturing speeds in capsule size 4 without the need for more complicated controlled wet granulation which additionally necessitates a need for drying. Surprisingly content uniformity is adequately maintained along with other performance parameters with a dry blending process at this lower particle size.

Example 2

| Sr. No | Ingredients | Quantity/Tablet (mg) |
|---|---|---|
| | Ia) Pre-lubrication | |
| 1 | Pimavanserin tartrate | 11.80 |
| 2 | Microcrystalline Cellulose | 133.2 |
| 3 | Colloidal silicon dioxide | 4.00 |
| | Ib) Lubrication | |
| 4 | Magnesium Stearate | 1.00 |
| | Core Tablet Weight (mg) | 150.00 |
| | II. Film-Coating | |
| 5 | Opadry ® AMB II | 7.80 |
| 6 | Purified water | q.s |
| | Coated Tablet Weight (mg) | 157.80 |

Processing solvent. Not present in the final product, except traces.
Opadry ® AMB II purple contains: Polyvinyl alcohol, Titanium dioxide and Talc, glycerol Monocaprylocaprate, sodium lauryl sulphate.

Manufacturing Procedure:
Core Tablet:
Step 1: Pimavanserin tartrate, Microcrystalline Cellulose and colloidal silicon dioxide were co-sifted.
Step 2: Materials of step 1 were milled with finer size mesh at desired speed.
Step 3: Magnesium Stearate was sifted separately.
Blending and Lubrication:
Step 4: Material of step 2 was loaded into suitable blender and then blended for 10 minutes.
Step 5: Material of step 4 was lubricated with step 3 material and blended for 5 minutes.

Compression:
Step 6: Lubricated blend of step 5 was compressed into tablets.
Coating:
Step 7: Opadry was dispersed into purified water with continuous stirring.
Step 8: The core tablets of step 6 were coated with aqueous dispersion of Opadry for desired weight gain.
The native amorphous pimavanserin tartrate of example 2 was having a particle size distribution (D90) of about 100 μm and the bulk density of 0.374 g/ml.

We claim:
1. A pharmaceutically acceptable capsule for orally delivering pimavanserin to a patient in need thereof, wherein said capsule encapsulates a stable pimavanserin composition comprising (i) amorphous pimavanserin tartrate having a particle size distribution with D90 of less than 200 μm as measured by laser light scattering and a bulk density of from 0.3 g/ml to 0.4 g/ml; and (ii) at least one pharmaceutically acceptable excipient selected from the group consisting of diluents, glidants, disintegrants, lubricants and combinations thereof; and wherein said stable pimavanserin composition is prepared by a dry blending process.

2. The pharmaceutically acceptable capsule of claim 1 comprising 40 mg of amorphous pimavanserin tartrate; 55 mg of microcrystalline cellulose as the diluent; and 4 mg of colloidal silicon dioxide as the lubricant.

3. The pharmaceutically acceptable capsule of claim 2, wherein said capsule is a size 3 capsule or a size 4 capsule.

4. The pharmaceutically acceptable capsule of claim 2 further comprising 1% w/w of magnesium stearate as the lubricant.

5. A process of preparing a pharmaceutically acceptable capsule for orally delivering 34 mg of pimavanserin, the process comprising the steps of:
(i) blending 40 mg of amorphous pimavanserin tartrate having a particle size distribution with D90 of from 75 μm to 200 μm as measured by laser light scattering and a bulk density of from 0.3 g/ml to 0.4 g/ml; 55 mg of microcrystalline cellulose; and 4 mg of colloidal silicon dioxide;
(ii) lubricating the blend of step (i) with 1 mg of magnesium stearate;
(iii) filling the blend of step (ii) into empty capsule shells.

* * * * *